(12) United States Patent
Corenman

(10) Patent No.: US 11,207,189 B2
(45) Date of Patent: Dec. 28, 2021

(54) BIOLOGICAL DISC GRAFT AND METHOD FOR RELIEF OF LOWER BACK PAIN AND JOINT PAIN

(71) Applicant: Donald Steven Corenman, Edwards, CO (US)

(72) Inventor: Donald Steven Corenman, Edwards, CO (US)

(*) Notice: Subject to any disclaimer, the term of this patent is extended or adjusted under 35 U.S.C. 154(b) by 0 days.

(21) Appl. No.: 16/438,438

(22) Filed: Jun. 11, 2019

(65) Prior Publication Data

US 2019/0321189 A1    Oct. 24, 2019

Related U.S. Application Data

(63) Continuation-in-part of application No. 14/925,602, filed on Oct. 28, 2015, now Pat. No. 10,314,720.

(60) Provisional application No. 62/153,164, filed on Apr. 27, 2015, provisional application No. 62/158,674, filed on May 8, 2015.

(51) Int. Cl.
*A61F 2/44* (2006.01)
*A61F 2/46* (2006.01)
*A61L 27/36* (2006.01)
*A61F 2/30* (2006.01)

(52) U.S. Cl.
CPC .......... *A61F 2/442* (2013.01); *A61F 2/4455* (2013.01); *A61F 2/4644* (2013.01); *A61L 27/3658* (2013.01); *A61F 2002/30476* (2013.01); *A61F 2002/443* (2013.01); *A61F 2002/444* (2013.01); *A61F 2002/448* (2013.01); *A61F 2310/00359* (2013.01); *A61L 27/3608* (2013.01); *A61L 27/3612* (2013.01); *A61L 27/3687* (2013.01); *A61L 27/3691* (2013.01); *A61L 2430/24* (2013.01); *A61L 2430/38* (2013.01)

(58) Field of Classification Search
CPC ............................. A61F 2/44; A61F 2/30756
See application file for complete search history.

(56) References Cited

U.S. PATENT DOCUMENTS 6,344,058 B1 * 2/2002 Ferree ................ A61L 27/3612
128/898

* cited by examiner

*Primary Examiner* — David W Bates
(74) *Attorney, Agent, or Firm* — Riverside Law LLP

(57) ABSTRACT

The invention provides a method of making a biological disc graft. In one embodiment, the biological disc graft is useful for treating back or neck pain. In one embodiment, the biological disc graft is useful for treating any joint pain. The invention also provides a method of implanting said biological disc graft in a way that is minimally invasive and less dangerous.

14 Claims, 13 Drawing Sheets

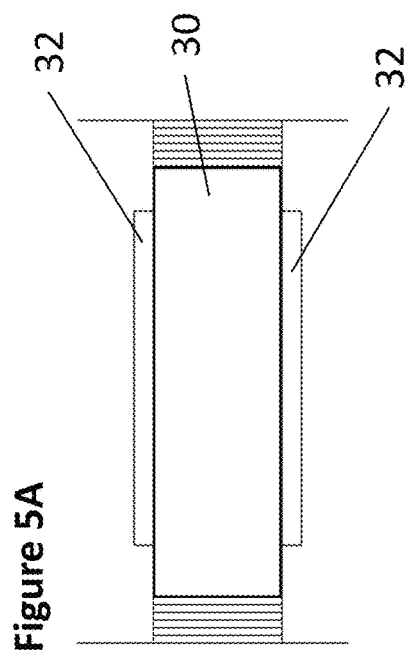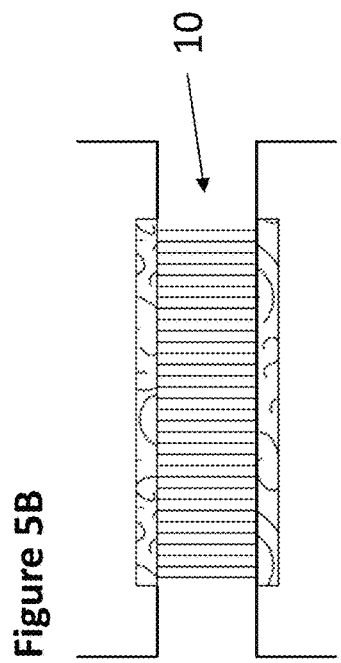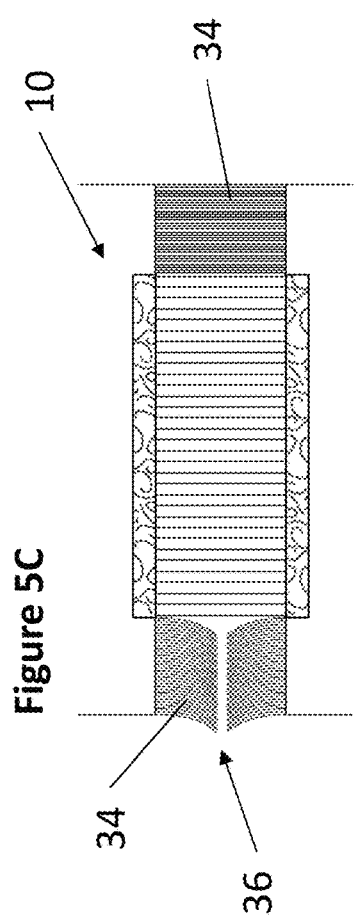

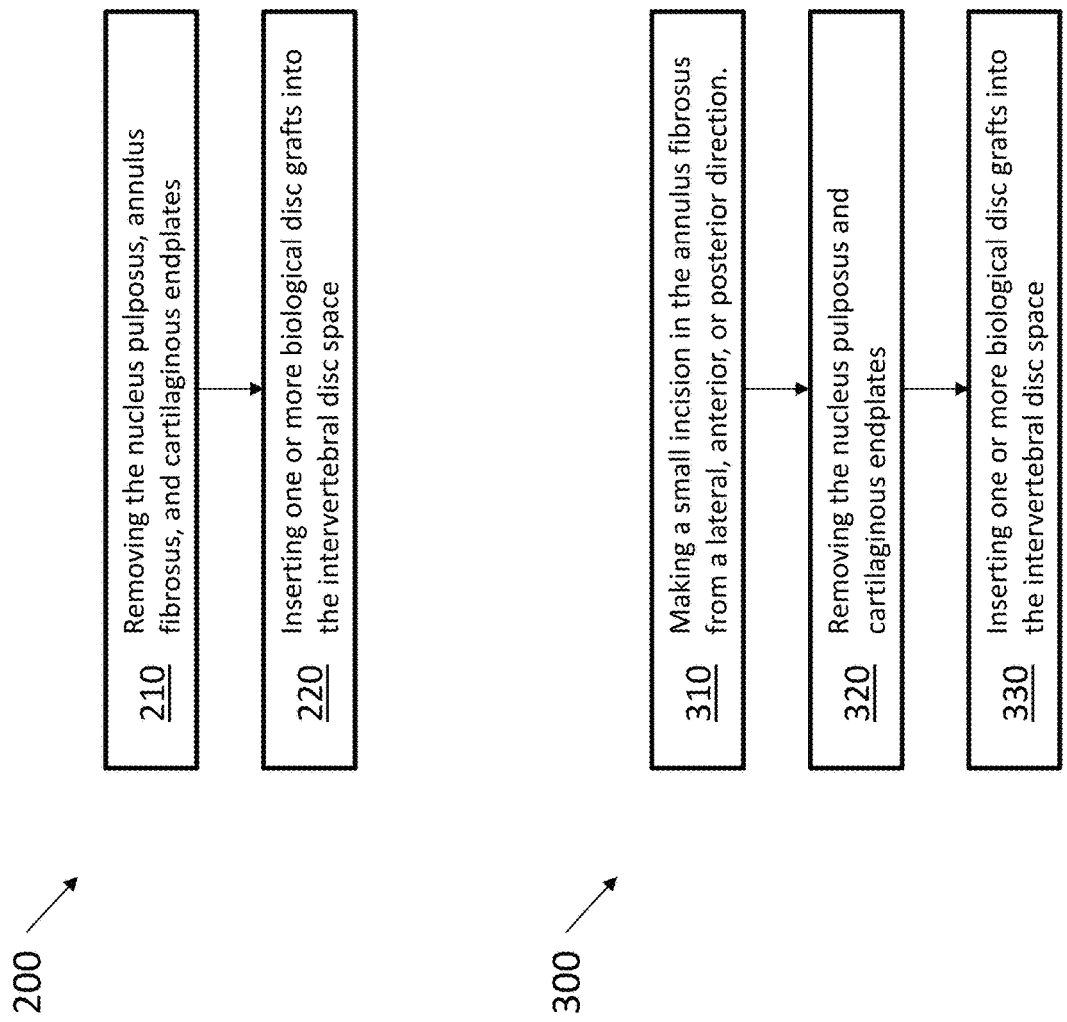

BIOLOGICAL DISC GRAFT AND METHOD FOR RELIEF OF LOWER BACK PAIN AND JOINT PAIN

CROSS-REFERENCE TO RELATED APPLICATIONS

This application is a continuation-in-part application of U.S. application Ser. No. 14/925,602, now allowed, which claims priority to U.S. Provisional Patent Application No. 62/153,164, filed Apr. 27, 2015, and to U.S. Provisional Patent Application No. 62/158,674, filed May 8, 2015, the contents of which are each incorporated by reference herein in their entirety.

BACKGROUND OF THE INVENTION

The normal discs of the spine are designed to absorb shock, but allow movement that places the spine in positions to help with the activities of daily living. Unfortunately, regions of the spine, including the lumbar spine and cervical spine, are often subjected to degenerative disc disease, resulting in the breakdown of the ability of the disc to absorb shock. This degeneration increases stress to the surrounding spine, especially in the bones of the vertebral body.

When this degeneration occurs, the increased stress can cause significant back and/or neck pain. The common method of surgically fusing the degenerative segment works well for pain relief but restricts motion, making the procedure less desirable.

Artificial disc replacement has been used for some years to reduce stress to the vertebral segment, while allowing some motion. However, a common problem with such replacements is that they must be implanted from the front of the spine, which necessitates an anterior approach to implant the artificial disc.

The anterior approach is fraught with potential complications, including scarring of the great vessels (aorta and vena cava), potential damage to the small and large intestines, the potential of retrograde ejaculation in males, damage to the ureters, and abdominal wall muscle injury. In addition, when these artificial discs fail, the approach to remove or replace them also requires the same anterior approach. In some instances, removal or replacement of these artificial discs can be life threatening.

Degeneration also occurs in various joints throughout the body. Either through age, disease, or physical injury, the layer of joint cartilage that cushions and lubricates joint movement wears away. Eventually, the cartilage is completely lost and the resulting bone-on-bone contact is extremely painful. While larger joints may benefit from cartilage grafts, smaller joints may require a joint fusion or a total artificial replacement.

Thus, there is an urgent need for an improved intervertebral disc replacement and method of implantation for safer, as well as more effective treatment of back, neck, and joint pain. The present invention addresses these needs.

SUMMARY OF THE INVENTION

A biological replacement disc graft is described. The graft includes first and second bone endplates, and a fibrocartilage layer positioned between the first and second bone endplates. In one embodiment, the fibrocartilage layer is between 1-10 mm thick. In another embodiment, the fibrocartilage layer comprises pubic symphysis. In another embodiment, the pubic symphysis is sourced from a human cadaver. In another embodiment, the bone and fibrocartilage layer are decellularized. In another embodiment, the bone endplates are milled to fit within the intervertebral disc space and engage the opposing vertebrae surfaces within the space. In another embodiment, the bone endplates are milled to fit within a joint space and engage the opposing bone surfaces within the space. In another embodiment, the joint is selected from the group consisting of: a carpometacarpal joint, a metacarpophalangeal joint, a interphalangeal joint, a metatarsal phalangeal joint, a wrist-bone articulation joint, a tarsal-metatarsal joint, a calcaneo-cuboid joint, a cuenonavicular joint, a acromio-clavicular joint, a sterno-clavicular joint, a spinal facet joint, a talar joint, a talonavicular joint, and a talo-calcaneal joint. In another embodiment, the graft further includes a push-to-lock mechanism in contact with at least one of the first and second bone endplates.

A method for making a biological disc graft is also described. The method includes the steps of isolating a pubic symphysis containing fibrocartilage from a cadaver, such that the fibrocartilage includes a portion of bone on both sides of the fibrocartilage, milling the isolated joint to a desired thickness and shape; and decellularizing the isolated joint. In one embodiment, the biological disc graft is milled to fit within the intervertebral disc space. In another embodiment, the method further includes the step of capping at least one of the bone portions with a push-to-lock mechanism. In another embodiment, the biological disc graft is milled to fit within a joint space. In another embodiment, the joint is selected from the group consisting of: a carpometacarpal joint, a metacarpophalangeal joint, a interphalangeal joint, a metatarsal phalangeal joint, a wrist-bone articulation joint, a tarsal-metatarsal joint, a calcaneo-cuboid joint, a cuenonavicular joint, a acromio-clavicular joint, a sterno-clavicular joint, a spinal facet joint, a talar joint, a talonavicular joint, and a talo-calcaneal joint.

A minimally invasive method for implanting a biological disc graft to treat back or neck pain is also described. The method includes the steps of making an incision in the annulus fibrosus of the intervertebral disc, removing a volume of nucleus pulposus equal to the volume of biological disc graft, and inserting the biological disc graft into the space previously occupied by the volume of nucleus pulposus. In one embodiment, the incision is made laterally, anteriorly, or posteriorly to the intervertebral disc.

A kit for use in the treatment of back, neck, or joint pain is also described. The kit includes at least one biological disc graft having first and second bone endplates, and a fibrocartilage layer positioned between the first and second bone endplates. In another embodiment, the kit includes at least one biological disc graft having one bone endplate and a fibrocartilage layer positioned adjacent to the one bone endplate.

A method for the total replacement of an intervertebral disc using the biological disc graft of the present invention is also described. The method includes the steps of removing the annulus fibrosus and nucleus pulposus of the intervertebral disc; removing cartilaginous endplates of the vertebral bodies above and below the intervertebral disc; and inserting the biological disc graft into the intervertebral disc space; wherein the bone endplates of the biological disc graft are seated in the space previously occupied by the cartilaginous endplates.

A method for the total replacement of a joint using the biological disc graft of the present invention is also described. The method includes the steps of removing cartilaginous endplates of the bones above and below the joint; and inserting the biological disc graft into the joint space.

BRIEF DESCRIPTION OF THE DRAWINGS

The following detailed description of preferred embodiments of the invention will be better understood when read in conjunction with the appended drawings. For the purpose of illustrating the invention, there are shown in the drawings embodiments which are presently preferred. It should be understood, however, that the invention is not limited to the precise arrangements and instrumentalities of the embodiments shown in the drawings.

FIG. 1A depicts the pubic symphysis in the pelvic bone. FIG. 1B depicts the cross-sectional shape of the pubic symphysis. FIG. 1C depicts a close-up view of the pubic symphysis joint with exemplary cut lines. FIG. 1D depicts the excised pubic symphysis joint with bone endplates prior to milling to shape.

FIG. 3A depicts top-down and side views of an exemplary intervertebral disc with surrounding vertebrae structures.

FIG. 3B depicts exemplary surgical entry points for inserting a biological disc graft that has been milled to shape.

FIG. 5A through FIG. 5C depicts exemplary techniques of implanting a biological disc graft into a subject's intervertebral disc space. FIG. 5A depicts the preparation of the intervertebral disc space. FIG. 5B depicts total disc replacement with annulus fibrosus removed. FIG. 5C depicts total disc replacement with annulus fibrosus preserved.

FIG. 6 is a flowchart depicting an exemplary method of repairing or replacing an intervertebral disc using a biological disc graft.

DETAILED DESCRIPTION

Figure 1A:
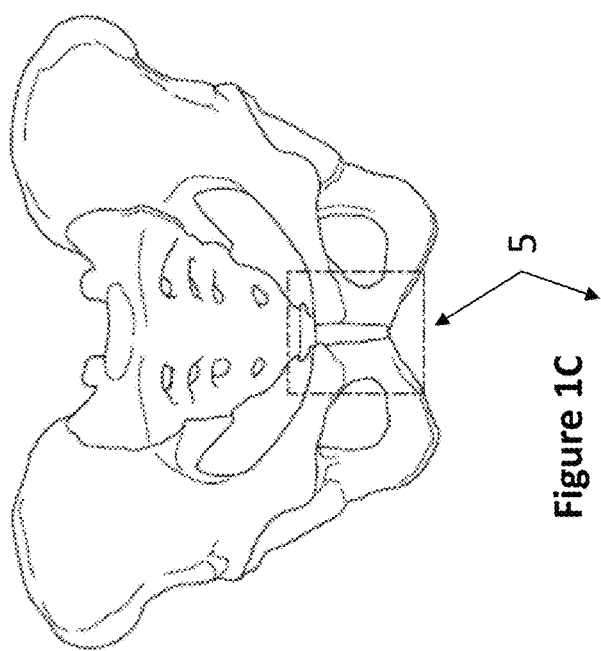
FIG. 1A through FIG. 1D depict a pubic symphysis joint before and after excision.

It is to be understood that the figures and descriptions of the present invention have been simplified to illustrate elements that are relevant for a clear understanding of the present invention, while eliminating, for the purpose of clarity, many other elements found in typical replacement disc grafts and methods of use. Those of ordinary skill in the art may recognize that other elements and/or steps are desirable and/or required in implementing the present invention. However, because such elements and steps are well known in the art, and because they do not facilitate a better understanding of the present invention, a discussion of such elements and steps is not provided herein. The disclosure herein is directed to all such variations and modifications to such elements and methods known to those skilled in the art.

Unless defined elsewhere, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are described.

As used herein, each of the following terms has the meaning associated with it in this section.

The articles "a" and "an" are used herein to refer to one or to more than one (i.e., to at least one) of the grammatical object of the article. By way of example, "an element" means one element or more than one element.

"About" as used herein when referring to a measurable value such as an amount, a temporal duration, and the like, is meant to encompass variations of ±20%, ±10%, ±5%, ±1%, and ±0.1% from the specified value, as such variations are appropriate.

As used herein, to "alleviate" a disease, defect, disorder, or condition means reducing the severity of one or more symptoms of the disease, defect, disorder, or condition.

As used herein, "biocompatible" refers to any material, which when implanted in a subject, does not provoke an adverse response in the subject. A biocompatible material, when introduced into an individual, is not toxic or injurious to that individual, nor does it induce immunological rejection of the material in the mammal.

As used herein, a "graft" refers to a cell, tissue, or organ that is implanted into an individual, typically to replace, correct, or otherwise overcome a defect. A graft may further comprise a scaffold. The cell, tissue, or organ may consist of cells that originate from the individual; this graft is referred to herein by the following interchangeable terms: "autograft", "autologous transplant", "autologous implant", and "autologous graft". A graft comprising cells from a genetically different individual of the same species is referred to herein by the following interchangeable terms: "allograft", "allogeneic transplant", "allogeneic implant", and "allogeneic graft". A graft from an individual to his identical twin is referred to herein as an "isograft", a "syngeneic transplant", a "syngeneic implant", or a "syngeneic graft". A "xenograft", "xenogeneic transplant", or "xenogeneic implant" refers to a graft from one individual to another of a different species.

As used herein, the term "grafting" refers to implanting a graft into an individual to treat or alleviate a defect, such as a tissue defect, bone defect, or joint defect.

"Growth factor" refers to a substance that is effective to promote the growth of cells. Growth factors include, but are not limited to, basic fibroblast growth factor (bFGF), acidic fibroblast growth factor (aFGF), epidermal growth factor (EGF), insulin-like growth factor-I (IGF-I), insulin-like growth factor-II (IGF-II), platelet-derived growth factor-AB (PDGF), vascular endothelial cell growth factor (VEGF), activin-A, bone morphogenic proteins (BMPs), insulin, cytokines, chemokins, morphogens, neutralizing antibodies, other proteins, and small molecules.

As used herein, the term "patient," "subject," "individual," and the like are used interchangeably herein, and refer to any animal, or cells thereof, whether in vitro or in situ, amenable to the methods described herein. In certain non-limiting embodiments, the patient, subject or individual is a mammal, non-limiting examples of which include a primate, dog, cat, goat, horse, pig, mouse, rat, rabbit, and the like, that is in need of bone formation. In some embodiments of the present invention, the subject is a human being. In such embodiments, the subject is often referred to as an "individual" or a "patient." The terms "individual" and "patient" do not denote any particular age.

As used herein, "scaffold" refers to a structure, comprising a biocompatible material that provides a surface suitable for adherence and proliferation of cells. A scaffold may further provide mechanical stability and support. A scaffold may be in a particular shape or form so as to influence or delimit a three-dimensional shape or form assumed by a population of proliferating cells. Such shapes or forms include, but are not limited to, films (e.g. a form with two-dimensions substantially greater than the third dimension), ribbons, cords, sheets, flat discs, cylinders, spheres, 3-dimensional amorphous shapes, etc.

As used herein, the term to "treat" means reducing the frequency with which symptoms of a disease, defect, disorder, or adverse condition, and the like, are experienced by a patient.

Throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6, etc., as well as individual numbers within that range, for example, 1, 2, 2.7, 3, 4, 5, 5.3, 6, and any whole and partial increments therebetween. This applies regardless of the breadth of the range.

The present invention includes biological disc grafts and methods of making and implanting the same. In one embodiment, the biological disc graft is useful for treating back pain or neck pain by inserting the disc graft between cervical, thoracic, or lumbar vertebrae. The present invention also includes improved methods of implanting intervertebral disc grafts, including the biological disc grafts described herein.

In one embodiment, the biological disc graft may be adapted for insertion into any joint. After insertion, the biological disc graft may reduce or eliminate pain, for instance pain from bone-on-bone contact in joints having cartilage loss. The biological disc may also restore the normal function of a joint having cartilage loss.

Referring now to FIG. 1A through FIG. 1D, an exemplary biological disc graft 10 and method of making the same is shown. Biological disc graft 10 is sourced from a cadaver joint 5 having a thin layer of fibrocartilage 12 adjoining two pieces of bone 14 forming bone endplates on either side of the fibrocartilage 12. Cadaver joint 5 may be from a mammalian cadaver, preferably a human cadaver. In one embodiment, the cadaver joint is a symphysis joint. In one embodiment, the cadaver joint is the pubic symphysis.

Figure 1B:
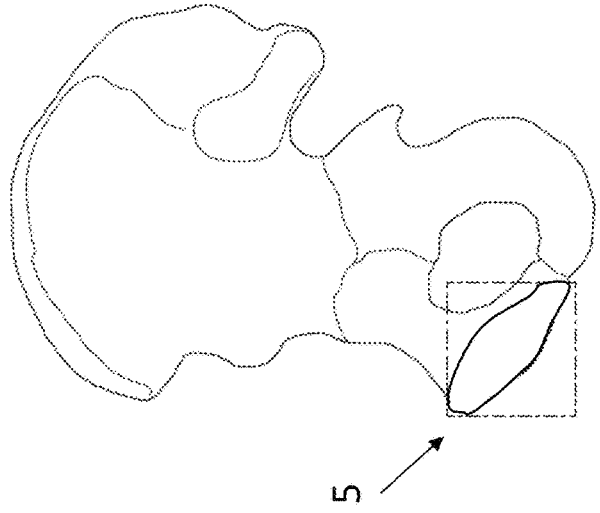

The pubic symphysis forms the union between the pubic bones of the pelvis (FIG. 1A). The joint comprises the medial surfaces of the pubic bones with an intervening fibrocartilaginous disc. The fibrocartilage disc meets the pubic bones at the articular surface, which is covered in hyaline cartilage varying between 200 μm to 3 mm in thickness, which decreases with age. The articular surfaces of the pubic bones are oval in shape, giving the same shape to the pubic symphysis (FIG. 1B). Adjacent to the articular surface is a layer of subchondral bone. The fibrocartilage disc comprises a broad mass of fibrocartilage tissue. The outer layers comprise obliquely running fibers that are thicker anteriorly. The vasculature of the surrounding bone extends from branches of the external and internal pudendal arteries and the medial circumflex artery. Small blood vessels may become more prominent within the disc with advancing age.

Those skilled in the art will recognize that the fibrocartilage in a pubic symphysis varies in width depending on the age of development in a subject. For example, a 3 year old human has a fibrocartilage width of about 10 mm, a 20 year old human has a fibrocartilage width of about 5 mm, and a 50 year old human has a fibrocartilage width of about 3 mm. In addition, women have wider fibrocartilage than men.

In women, the fibrocartilage experiences additional changes during pregnancy. In one aspect, the fibrocartilage width increases, from an average of 4-6 mm before pregnancy to 6-8 mm in the last two months of pregnancy. The widening of the fibrocartilage is accompanied by a higher water content. The changes are in part affected by increased levels of relaxin and estrogen, which play a role in collagen degradation and remodeling.

Figure 1C:
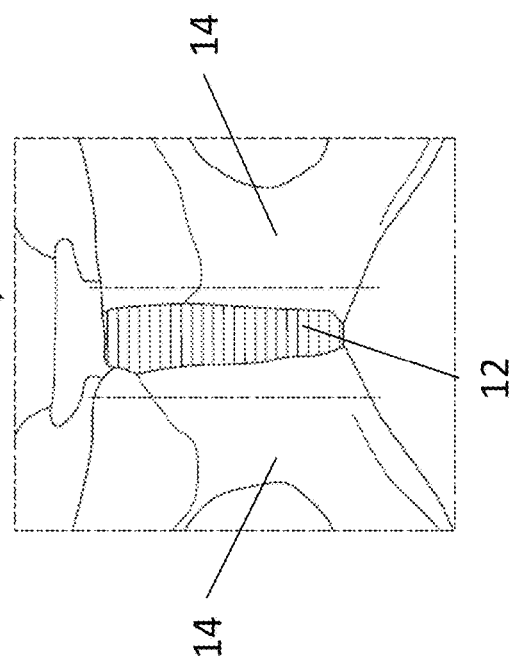
Figure 1D:
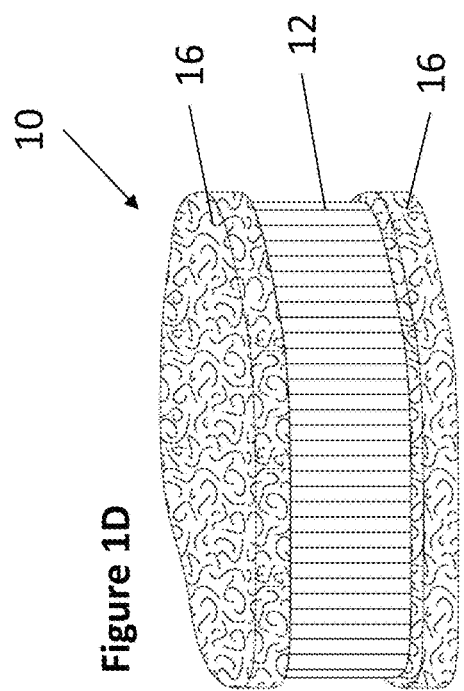

Fibrocartilage 12 is preferably removed from a cadaver with a layer of bone still attached on both sides as bone endplates 16, for example as depicted by cut lines shown in FIG. 1C. Once removed, fibrocartilage 12 with bone endplates 16 forms the basis of graft 10, which can later be milled to a shape and thickness appropriate for the recipient of the biological disc graft 10 (FIG. 1D). As contemplated herein, any standard tools for cutting, grinding and resurfacing bone may be used to achieve the desired size and shape of the biological disc graft.

In certain embodiments, fibrocartilage 12 may be removed from the cadaver with only one bone endplate 16 attached on one side. A biological disc graft having only one bone endplate 16 on one side can achieve a thinner profile than a biological disc graft having bone endplates 16 on both sides of fibrocartilage 12. A biological disc graft having only one bone endplate 16 is suitable for insertion into thin joint spaces. For instance, non-limiting examples of thin joint spaces may have widths that are less than 10 mm, less than 5 mm, or less than 3 mm. Non-limiting examples of joint spaces suitable for treatment using the biological disc graft of the present invention include carpometacarpal joints, metacarpophalangeal joints, interphalangeal joints, metatarsal phalangeal joints, wrist-bone articulation joints, tarsal-metatarsal joints, calcaneo-cuboid joints, cuenonavicular joints, acromio-clavicular joints, sterno-clavicular joints, spinal facet joints, talar joints, talonavicular joints, talocalcaneal joints, and the like.

In one embodiment, biological disc graft 10 can be treated to remove cellular material. For example, any bone attached to the biological disc graft may be decellularized. Decellularization of the biological disc graft, or a portion thereof as described herein, removes most or all of the cellular components while substantially preserving the extracellular matrix (ECM) and other structures, e.g. vascular structures, Haversian canals, Volkmann's canals, lacunae, lamellae, canaliculi, osteon, periosteum, trabeculae, and combinations thereof.

Bones include four major types of cells that are removed by decellularization methods, including osteoblasts, osteocytes, bone-lining cells, and osteoclasts. Osteoblasts are mononucleate bone-forming cells that descend from osteoprogenitor cells. They are located on the surface of osteoid seams and make a protein mixture known as osteoid, which mineralizes to become bone. Osteoid is primarily composed of Type I collagen. Osteoblasts also manufacture hormones, such as prostaglandins, to act on the bone itself; alkaline phosphatase, an enzyme that has a role in the mineralisation of bone; as well as many matrix proteins. Osteoblasts are the immature bone cells, and eventually become entrapped in the bone matrix to become osteocytes, the mature bone cell. Osteocytes originate from osteoblasts that have migrated into and become trapped and surrounded by bone matrix that they themselves produce. The spaces they occupy are known as lacunae. These cells primarily sense mechanical load or tissue damage and subsequently can initiate remodeling responses. Osteocyte functions include formation of bone, matrix maintenance, and calcium homeostasis. Bone-lining cells, which cover resting bone surfaces, also share mechanosensation and adaptation duties. Lining cells can differentiate into an "osteoblastic" state as well as recruit osteoprogenitor cells.

Additionally, lining cells are also instrumental in bone resorption by recruiting osteoclasts (bone resorption cells) to resorption sites; boosting the differentiation of osteoclast precursors; and preparing the bone surface for resorption. Osteoclasts are the cells responsible for bone resorption, thus they break down bone. New bone is then formed by the osteoblasts (remodeling of bone to reduce its volume). Osteoclasts are large, multinucleated cells located on bone surfaces in what are called Howship's lacunae or resorption pits. These lacunae, or resorption pits, are left behind after the breakdown of the bone surface.

The majority of bone is made of the bone matrix. It has inorganic and organic parts. The inorganic composition of bone (bone mineral) is formed from carbonated hydroxyapatite ($Ca_{10}(PO_4)_6(OH)_2$) with lower crystallinity. The organic part of the matrix is mainly composed of Type I collagen. This is synthesized intracellularly as tropocollagen and then exported to form fibrils. The organic part is also composed of various growth factors, including glycosaminoglycans, osteocalcin, osteonectin, bone sialo protein, osteopontin, and cell attachment factor.

Those skilled in the art will recognize that any known method of decellularizing tissue may be used to remove cellular material from biological disc graft 10. For instance, one method of decellularizing tissue involves soaking harvested tissue in hyaluronidase (type IV-s, 3 mg/mL) and trypsin (0.25% in monodibasic buffer 3 ml) for about 18 hours at 37° C. with optional sonication. Harvested tissue can then be decalcified and repeatedly washed with deionized water and placed in a 50%/50% chloroform/methanol solution for 72 hours to remove cellular debris and to sterilize. Alternatively or additionally, the harvested tissue may be frozen.

In one embodiment, the decellularized biological disc graft is seeded with one or more populations of cells. The cell populations may be autologous, derived from the subject's own tissue, or allogenic, derived from another human subject. The cell populations may also be xenogenic, where the cells are derived from a mammalian species that is different. Cells can be isolated from a number of sources, such as biopsies from living subjects and whole-organ recovery from cadavers. The isolated cells are preferably autologous cells, obtained by biopsy from the subject intended to be the recipient.

Cells may be isolated using techniques known in the art. For example, the tissue or organ can be disaggregated mechanically and/or treated with digestive enzymes and/or chelating agents that weaken the connections between neighboring cells making it possible to disperse the tissue into a suspension of individual cells without appreciable cell breakage. Enzymatic dissociation can be accomplished by mincing the tissue and treating the minced tissue with any of a number of digestive enzymes either alone or in combination. These include but are not limited to trypsin, chymotrypsin, collagenase, elastase, and/or hyaluronidase, DNase, pronase and dispase. Mechanical disruption can also be accomplished by a number of methods including, but not limited to, scraping the surface of the organ, the use of grinders, blenders, sieves, homogenizers, pressure cells, or insonicators. Preferred cell types include, but are not limited to, fibroblasts, chondrocytes, osteoblasts, and other cells forming bone or cartilage.

Once the tissue has been reduced to a suspension of individual cells, the suspension can be fractionated into subpopulations from which the cells elements can be obtained. This also may be accomplished using standard techniques for cell separation including, but not limited to, cloning and selection of specific cell types, selective destruction of unwanted cells (negative selection), separation based upon differential cell agglutinability in the mixed population, freeze-thaw procedures, differential adherence properties of the cells in the mixed population, filtration, conventional and zonal centrifugation, centrifugal elutriation (counterstreaming centrifugation), unit gravity separation, countercurrent distribution, electrophoresis and fluorescence-activated cell sorting.

Proliferation of seeded cells or infiltration of a patient's native cells in the biological disc graft may be aided with the addition of natural materials, synthetic materials, or combinations thereof. Examples include but are not limited to amino acids, peptides, denatured peptides such as gelatin from denatured collagen, polypeptides, proteins, carbohydrates, lipoids, nucleic acids, glycoproteins, lipoproteins, glycolipids, glycosaminoglycans, and proteoglycans. Additional materials include naturally occurring extracellular matrix materials and blends of naturally occurring extracellular matrix materials, including but not limited to collagen, fibrin, fibrinogen, thrombin, elastin, laminin, fibronectin, hyaluronic acid, chondroitin 4-sulfate, chondroitin 6-sulfate, dermatan sulfate, heparin sulfate, heparin, and keratin sulfate. Some collagens that are used include but are not limited to collagen types I, II, III, IV, V VI, VII, VIII, IX, X, XI, XII, XIII, XIV, XV, XVI, VII, XVIII, and XIX. These proteins may be in any form, including but not limited to native and denatured forms. Other materials are carbohydrates such as polysaccharides (e.g. cellulose and its derivatives), chitin, chitosan, alginic acids, and alginates such as calcium alginate and sodium alginate. These materials may be isolated from plant products, humans, or other organisms or cells or synthetically manufactured. Also included are crude extracts of tissue, extracellular matrix materials, or combinations thereof. Extracts of biological materials include but are not limited to cells, tissues, and organs.

The synthetic materials may include any materials prepared through any method of artificial synthesis, processing, isolation, or manufacture. The synthetic materials are preferably biologically compatible for administration in vivo or in vitro. Such polymers include but are not limited to the following: poly(urethanes), poly(siloxanes) or silicones, poly(ethylene), poly(vinyl pyrrolidone), poly(2-hydroxy ethyl methacrylate), poly(N-vinyl pyrrolidone), poly(methyl methacrylate), poly(vinyl alcohol), poly(acrylic acid), polyacrylamide, poly(ethylene-co-vinyl acetate), poly(ethylene glycol), poly(methacrylic acid), polylactic acid (PLA), polyglycolic acids (PGA), poly(lactide-co-glycolides) (PLGA), nylons, polyamides, polyanhydrides, poly(ethylene-co-vinyl alcohol) (EVOH), polycaprolactone, poly(vinyl acetate) (PVA), polyvinylhydroxide, poly(ethylene oxide) (PEO) and polyorthoesters or any other similar synthetic polymers that may be developed that are biologically compatible. The polymers may have any molecular structure including, but not limited to, linear, branched, graft, block, star, comb, and dendrimer structures.

In one embodiment, the biological disc graft may be enhanced with the introduction of combinations of natural materials, combinations of synthetic materials, and combinations of both natural and synthetic materials. Examples of combinations include, but are not limited to: blends of different types of collagen (e.g. Type I with Type II, Type I with Type III, Type II with Type III, etc.); blends of one or more types of collagen with fibrinogen, thrombin, elastin, PGA, PLA, and polydioxanone; and blends of fibrinogen with one or more types of collagen, thrombin, elastin, PGA, PLA, and polydioxanone.

Figure 2:
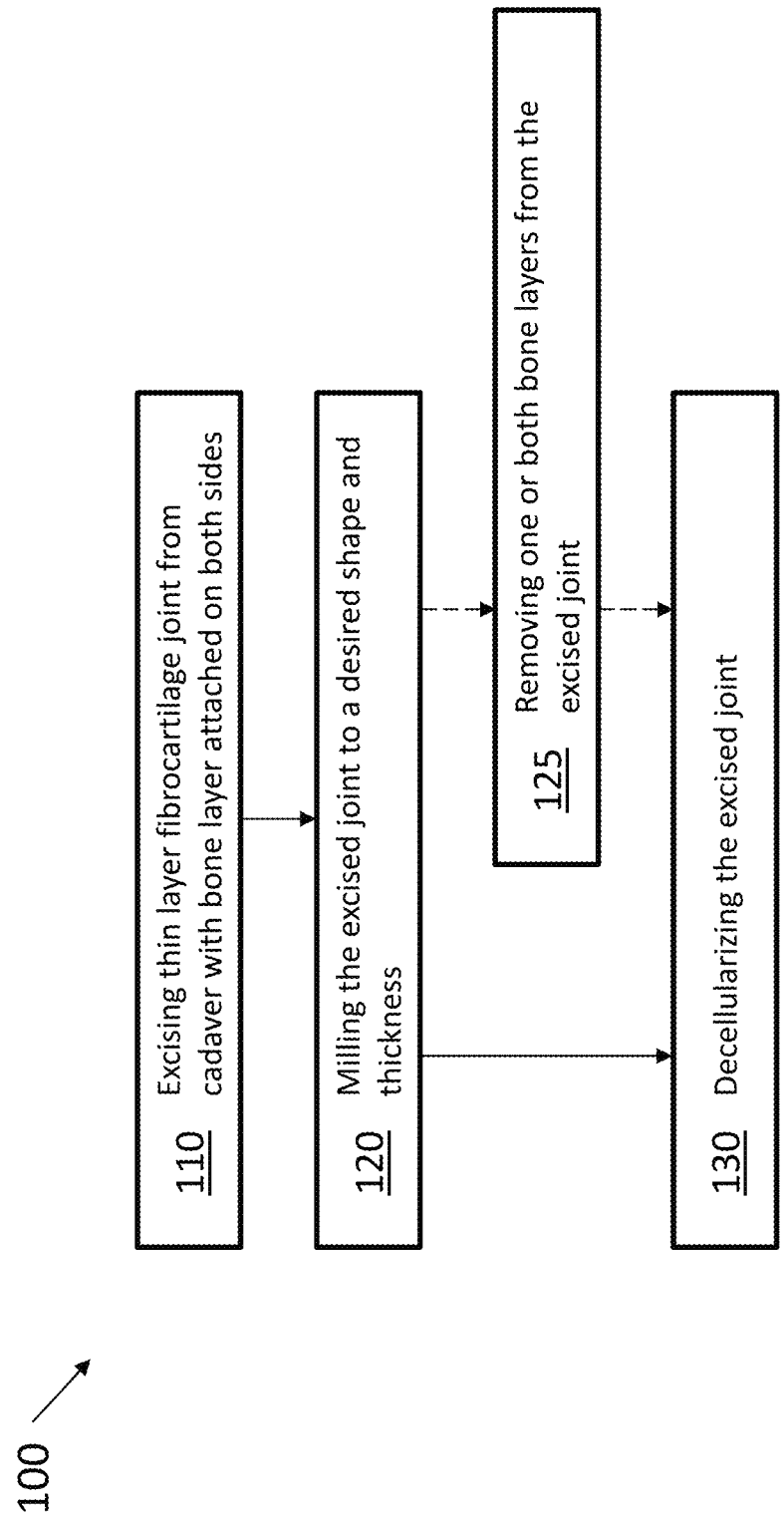
FIG. 2 is a flowchart depicting an exemplary method of making a biological disc graft.

Referring now to FIG. 2, an exemplary method 100 of making a biological disc graft is summarized. The method begins with step 110, where a thin layer fibrocartilage joint is excised from a cadaver with a bone layer attached on both sides. Next, in step 120, the excised joint is milled to a desired shape and thickness. Optionally, in step 125, one or both bone layers is removed to suit the application of the biological disc graft. In step 130, to improve biocompatibility, the excised joint is decellularized.

In one embodiment, biological disc graft 10 may be capped with a push-to-lock mechanism. The push-to-lock mechanism enables two biological disc grafts to mechanically lock to one another. The push-to-lock mechanism may be any mechanism that secures one component to another upon pushing the two components against each other, such as a touch latch, or a magnetic mechanism, or any other mechanism that secures two components upon contact. The push-to-lock mechanism is especially advantageous in situations where the two biological disc grafts are in a location that makes then difficult to manipulate, such as within a joint space.

The biological disc grafts of the present invention are suitable for implantation into the intervertebral disc space for the reduction or elimination of back or neck pain. The intervertebral disc comprises mainly two structures, the nucleus pulposus at the core of the disc, and the annulus fibrosus forming the perimeter of the disc. The annulus fibrosus comprises individual lamellae primarily composed of collagen type I fibers. The nucleus pulposus consists of a proteoglycan/water gel loosely held together by a network of collagen type II and elastin fibers. The nucleus pulposus, with its high water content, provides compressive resistance and recovery with its ability to release and reabsorb water with the loading and unloading of compressive forces. The annulus fibrosus provides the tensile force to restrain the nucleus pulposus and maintain its shape and structure within the intervertebral disc space.

The outermost layer of the annulus fibrosus is innervated by the sinuvertebral nerve. Accordingly, back and neck pain occur in the event of disc prolapse, disc narrowing, radial fissures, and internal disc disruption. These can be caused by physical trauma, or with the weakening of the intervertebral disc as it degenerates over time. Annulus tears, radial fissures, and disc prolapse are frequently associated with trauma. Collapse of the inner annulus, disc narrowing, and disc bulging are frequently characterized as age-related. Years of repeated loading and unloading lead to the loss of nucleus pulposus pressure, either from the degeneration of the proteoglycans, or from the bulging of the nucleus pulposus into the vertebral bodies. The loss of pressure collapses the annulus fibrosus height, causing compressive forces to be felt by the disc nerve endings. Additional sources of pain include endplate fractures and Schmorl nodes (bone protrusions from the vertebra into the intervertebral disc).

The injured or degenerated intervertebral disc can be supplemented or replaced with the biological disc graft of the present invention for the reduction or elimination or back or neck pain. In one embodiment, the invention provides methods for total disc replacement.

Figure 3B:
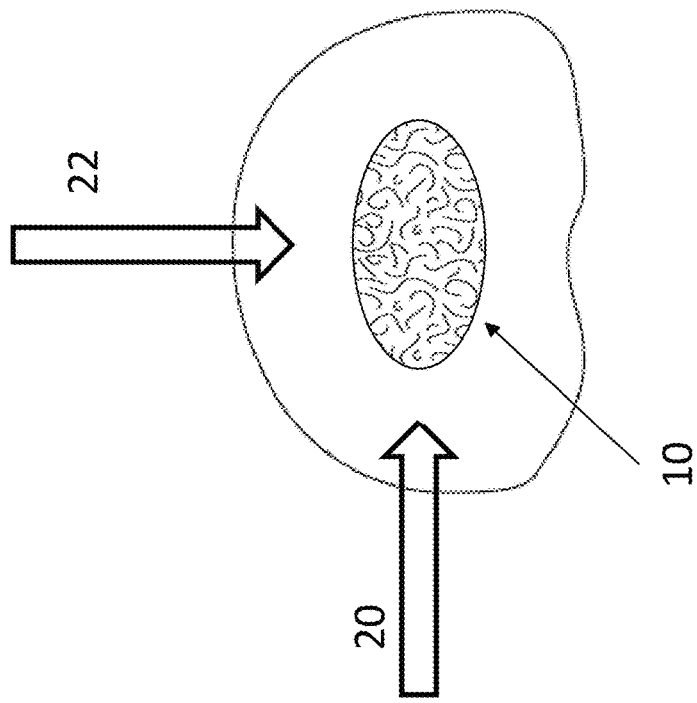
FIG. 3A and FIG. 3B depict exemplary methods of biological disc graft entry into a subject's intervertebral disc space.
Figure 3A:
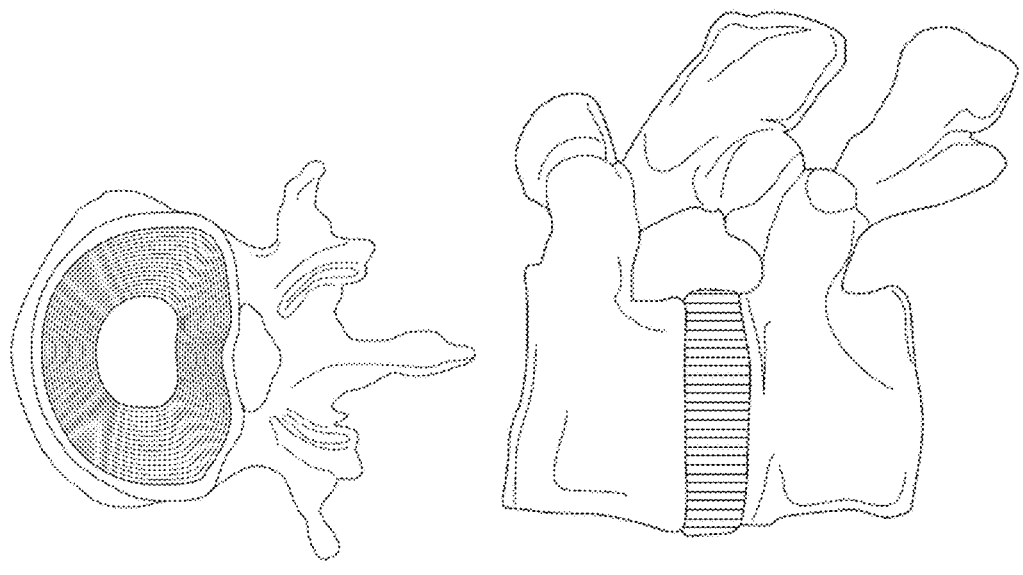
Figure 4:
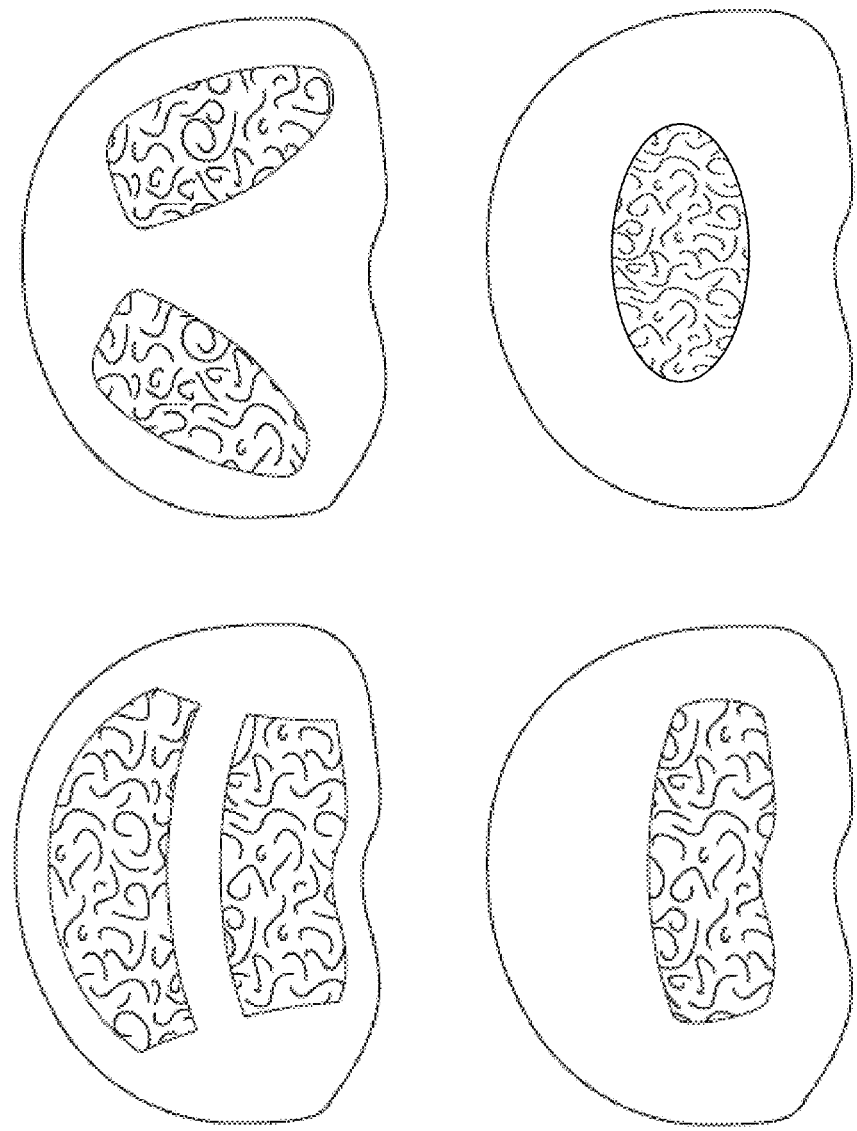
FIG. 4 depicts variations of biological disc graft implant orientations within the intervertebral disc space.
Figure 7:
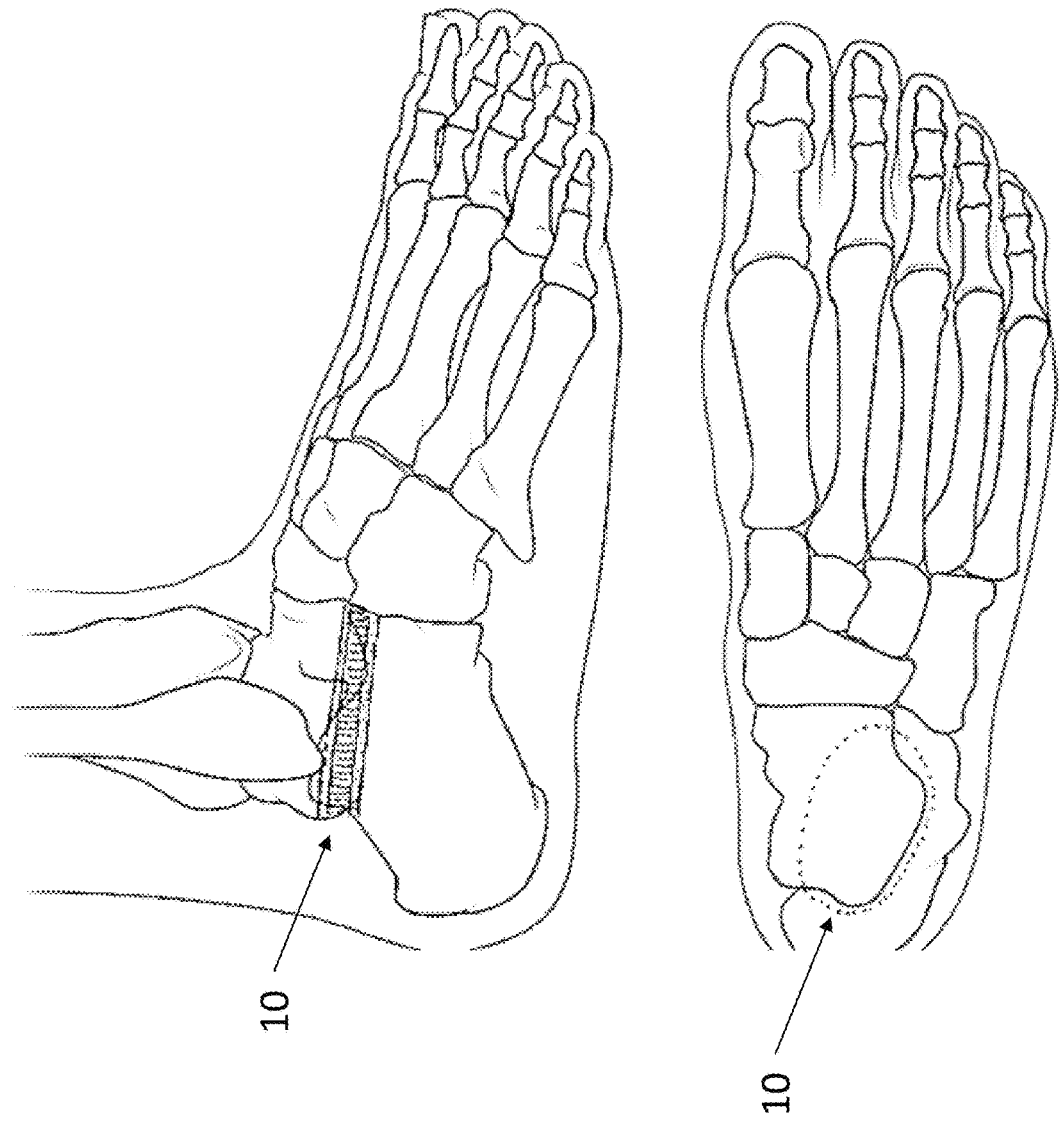
FIG. 7 depicts an exemplary talo-calcaneal joint graft.
Figure 8:
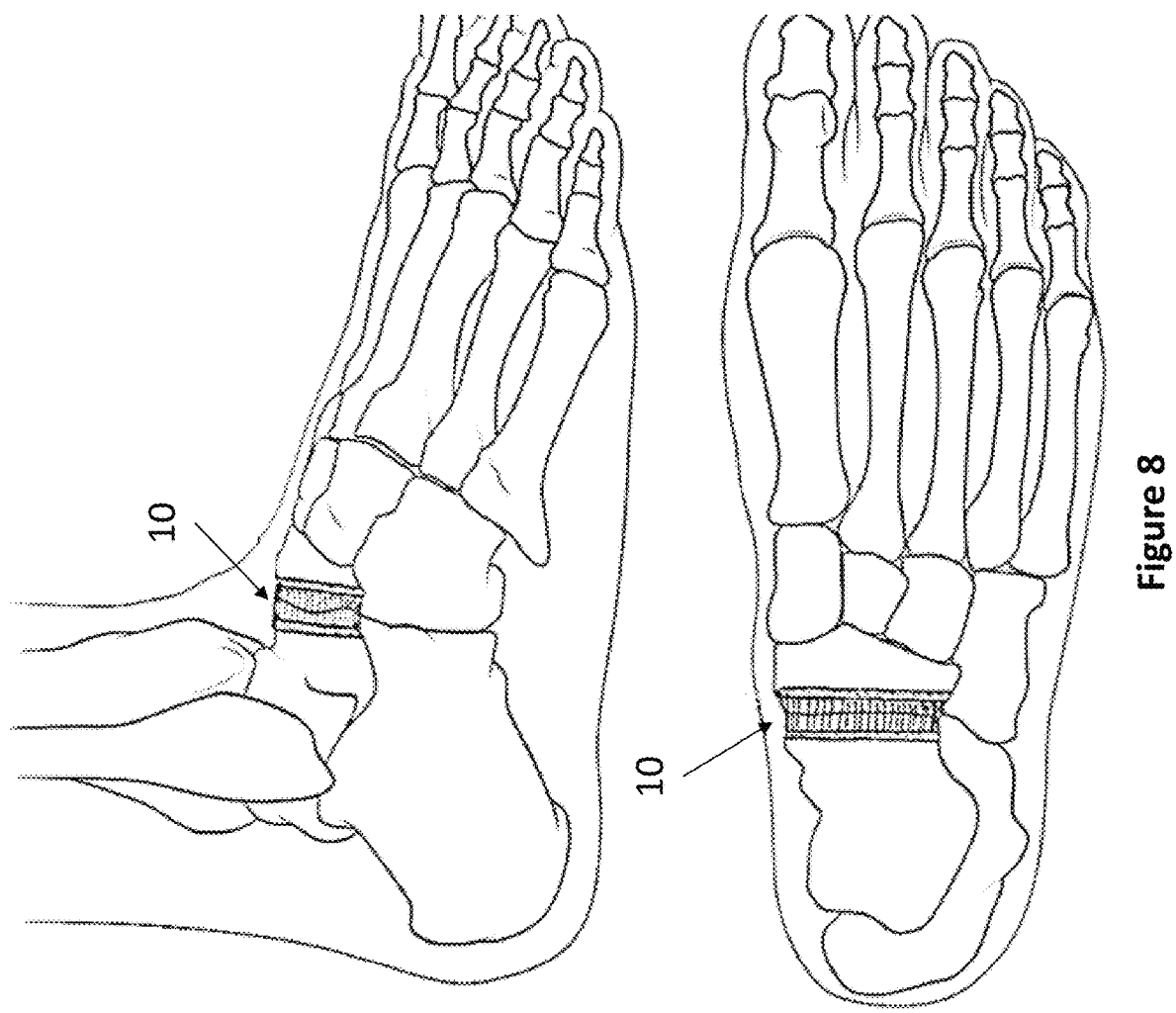
FIG. 8 depicts an exemplary talonavicular joint graft.
Figure 9:
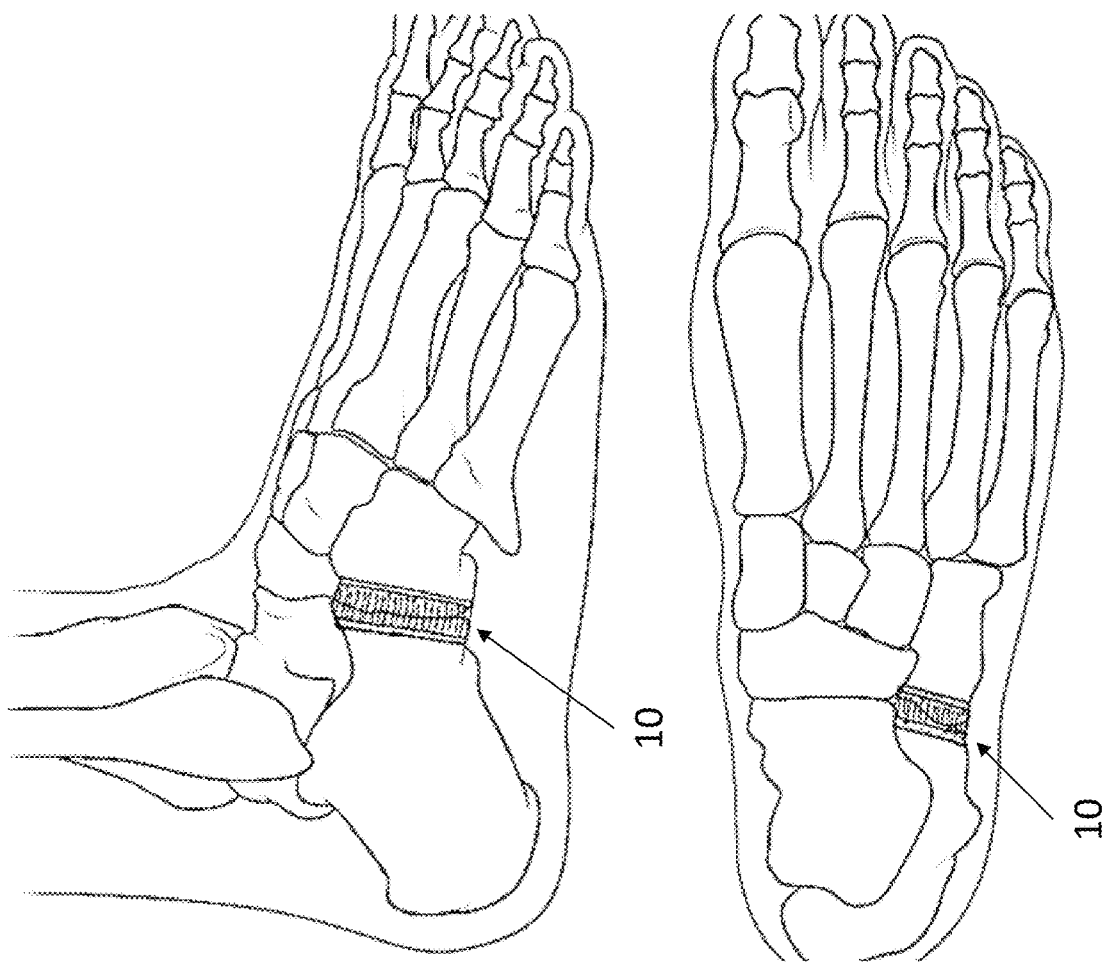
FIG. 9 depicts an exemplary calcaneo-cuboid joint graft.
Figure 10:
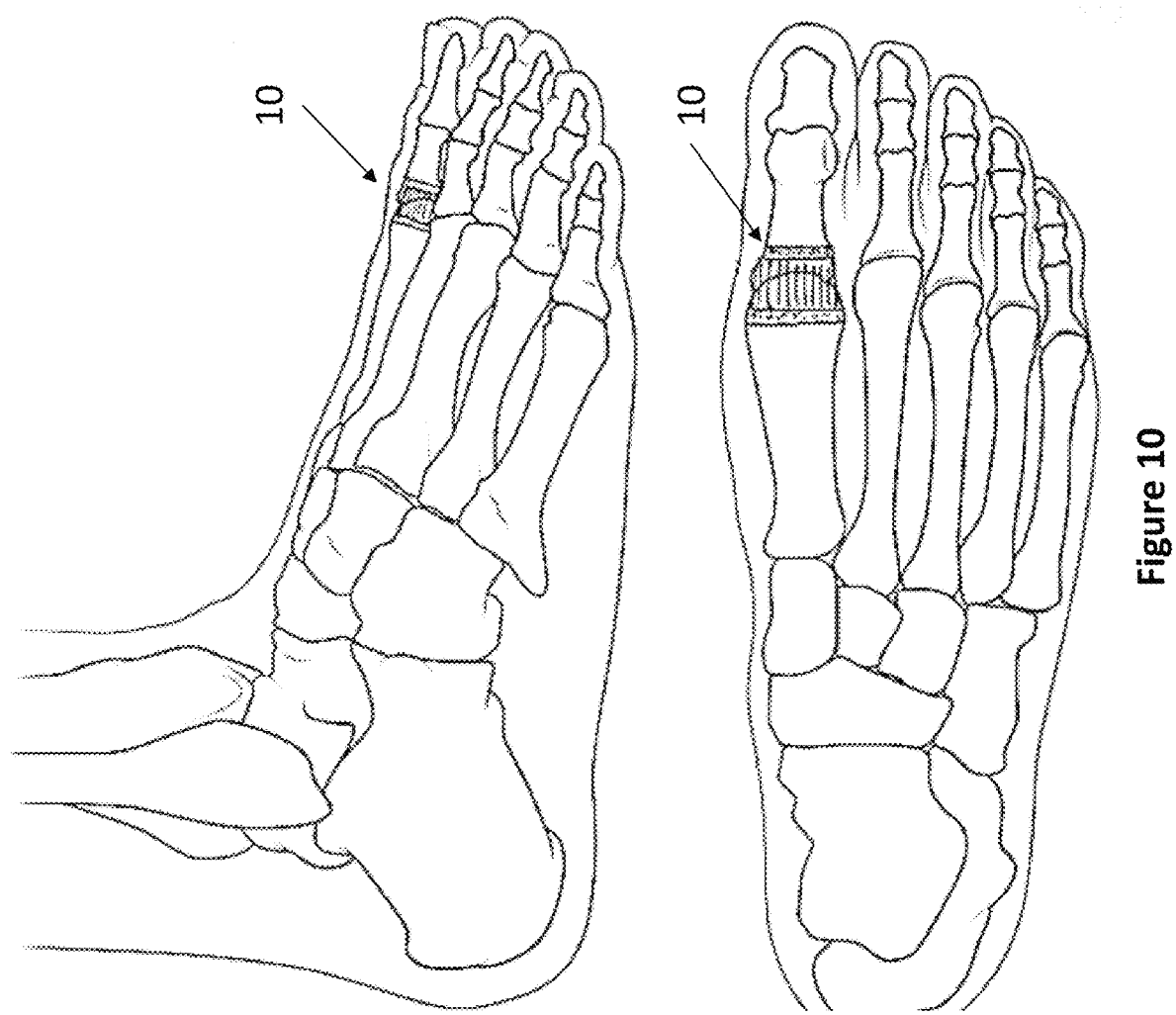
FIG. 10 depicts an exemplary tarsal-metatarsal joint graft.
Figure 11:
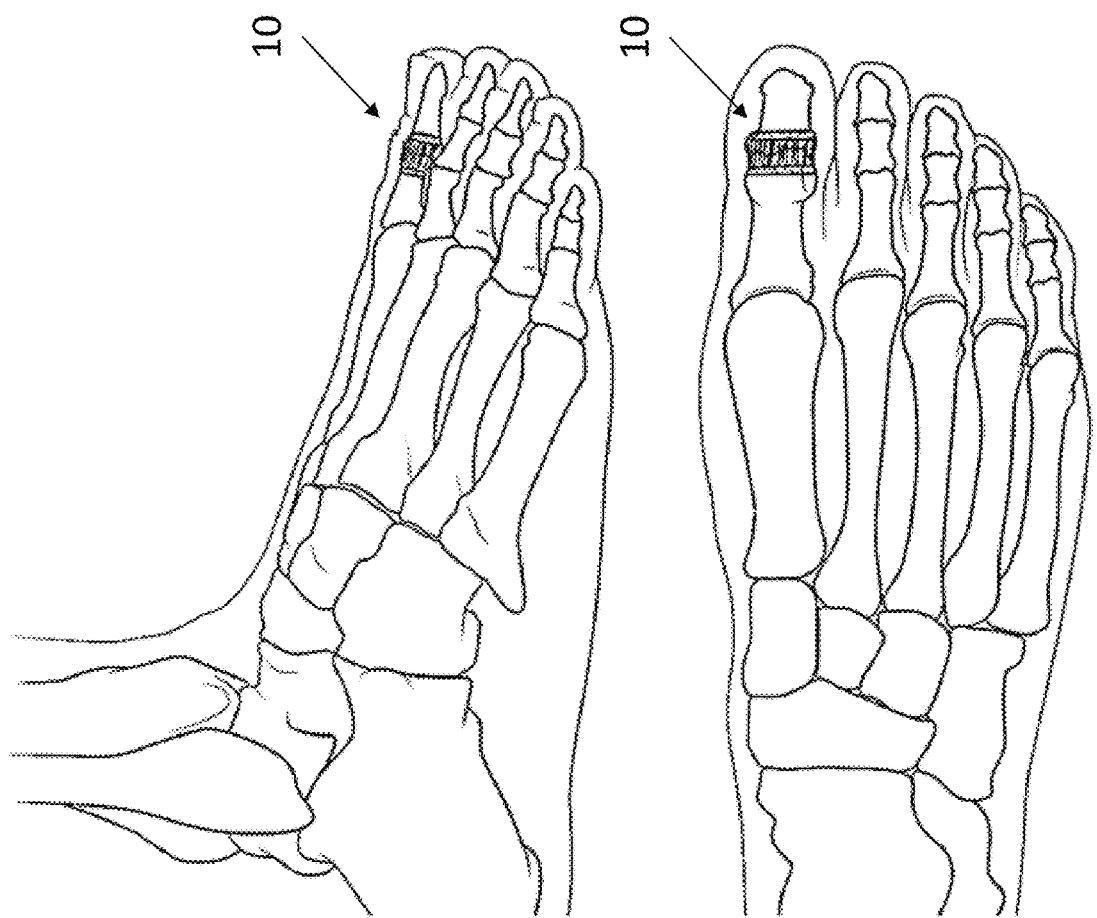
FIG. 11 depicts an exemplary interphalangeal joint graft.
Figure 12:
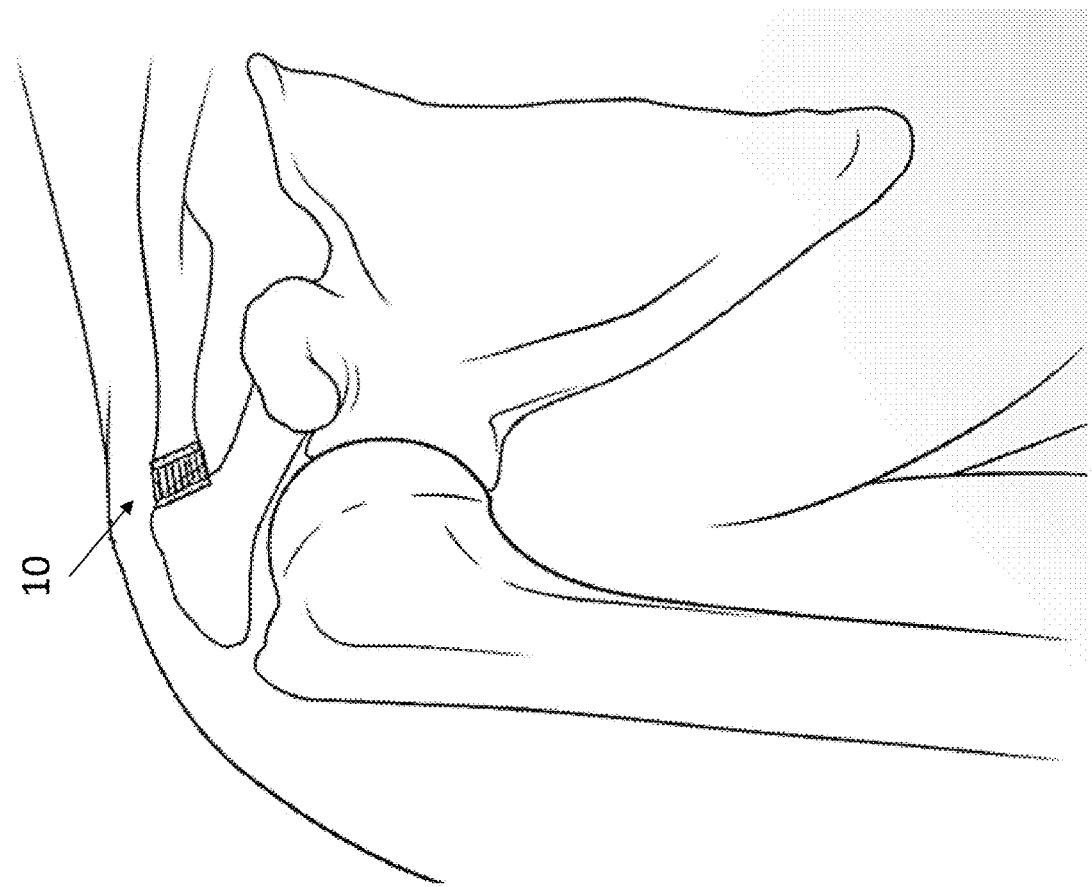
FIG. 12 depicts an exemplary acromio-clavicular joint graft.
Figure 13:
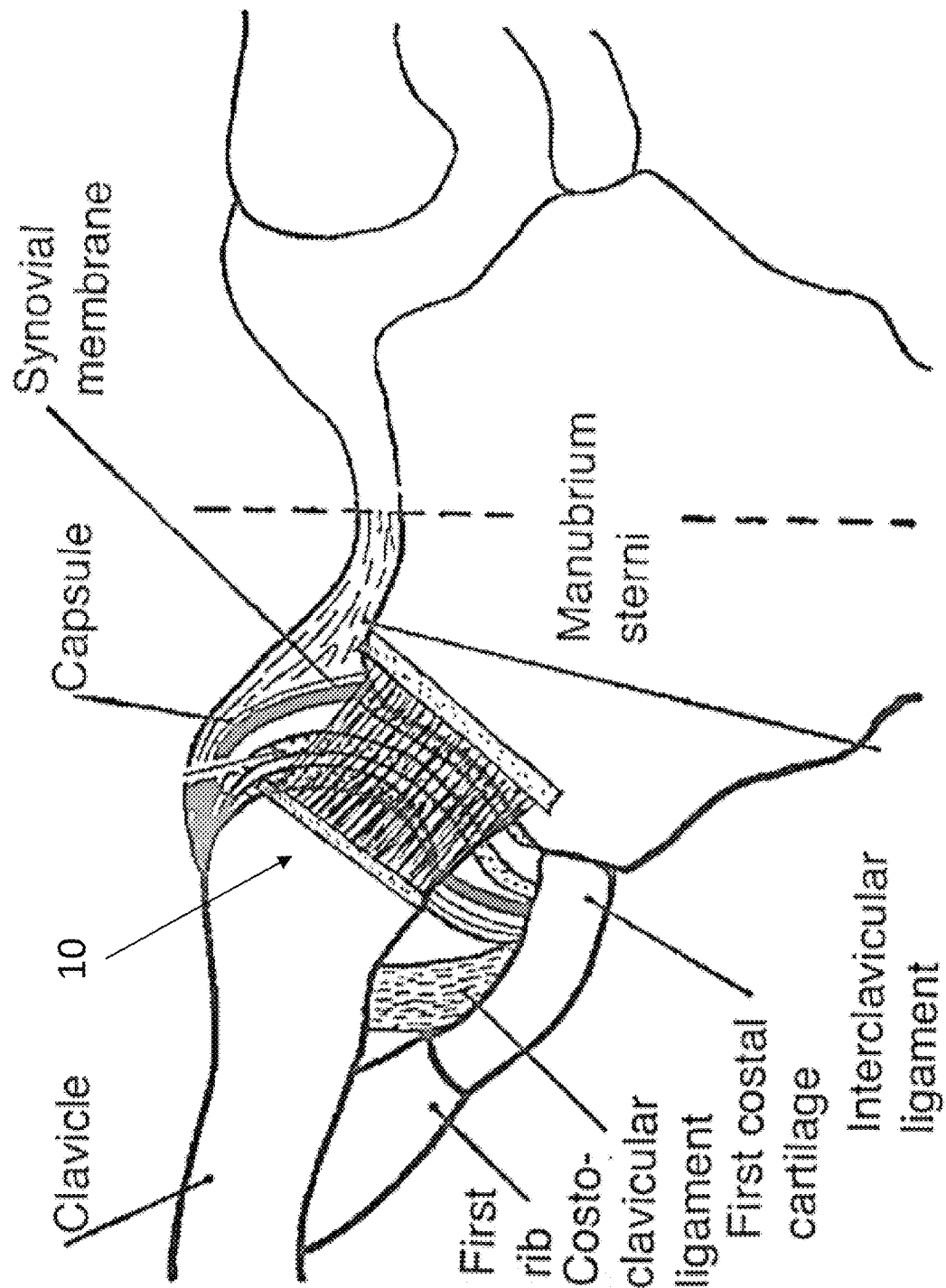
FIG. 13 depicts an exemplary sterno-clavicular joint graft.

Referring now to FIG. 3A, FIG. 3B, and FIG. 4, exemplary variations of implanting the biological disc grafts of the present invention are shown. While the invention contemplates the standard method of implanting artificial discs from an anterior direction, the present invention also makes use of small incisions in the annulus fibrosus from a directly lateral direction 20 or from a posterior direction 22 (FIG. 3B). The incision is just large enough to permit entry for a biological disc graft. After the incision is made, a volume of nucleus pulposus approximately equal to the volume of a biological disc graft is removed, and the disc graft is inserted in its place. In one embodiment, a plurality of grafts may be implanted into one intervertebral disc space (FIG. 4). The biological disc graft may also include one or more holes, recesses, grooves or pockets for engaging an insertion tool, such that the insertion tool can suitably engage, position and release the biological disc graft through the small incision.

In any method of the present invention where incisions are made in the annulus fibrosus, the incisions are intended to preserve as much of the natural structure of the annulus fibrosus as possible. Preferably, the angle of approach when making incisions are from a directly lateral direction or from a posterior direction avoids the facet joints of the spine. Furthermore, implanting the grafts of the present invention from a directly lateral direction or from a posterior direction avoids disturbing the great vessels, decreasing risk to the patient if it is necessary to remove the grafts from an anterior direction.

Referring now to FIG. 5A through FIG. 5C, exemplary illustrations of total disc replacement using the biological disc grafts of the present invention are shown. The methods of implanting begins with FIG. 5A, where the intervertebral disc space is prepared prior to receiving a biological disc graft. The nucleus pulposus 30 is removed in its entirety, as well as the cartilaginous endplates 32 of the vertebral bodies directly above and below the intervertebral disc space.

In FIG. 5B, the annulus fibrosus is completely removed. This may be suitable in situations where a subject's annulus fibrosus displays extreme degeneration or damage. The biological disc graft is inserted into the intervertebral disc space, with the bone endplates seated in the space previously occupied by the cartilaginous endplates.

In FIG. 5C, the annulus fibrosus 34 is substantially preserved. This may be suitable in situations where a subject's annulus fibrosus is still healthy. A small incision 36 is made in the annulus fibrosus such that the biological disc graft is able to pass through the incision. Like in FIG. 5B, the bone endplates of the biological disc graft are seated in the space previously occupied by the cartilaginous endplates.

Accordingly, FIG. 6 depicts exemplary methods 200 and 300 of repairing or replacing an intervertebral disc using the biological disc graft of the present invention. Method 200 begins with step 210, where the nucleus pulposus, annulus fibrosus, and cartilaginous endplates are removed from the patient's intervertebral disc. In step 220, one or more biological disc grafts are inserted into the intervertebral disc space. Method 300 begins with step 310, where a small incision is made in a patient's annulus fibrosus from a lateral, anterior, or posterior direction. In step 320, the nucleus pulposus and cartilaginous endplates are removed from the patient's intervertebral disc. In step 330, one or more biological disc grafts are inserted into the intervertebral disc space.

As described elsewhere herein, the biological disc graft 10 of the present invention is amenable for replacement of any suitable joint in a subject's body. Referring now to FIG. 7 through FIG. 12, exemplary replacement joints are depicted wherein a biological disc graft 10 has been milled to fit within a talo-calcaneal joint space, a talonavicular joint space, a calcaneo-cuboid joint space, a tarsal-metatarsal joint space, an interphalangeal joint space, an acromio-clavicular joint space, and a sterno-clavicular joint space, respectively. Additional replacement joints, while not pictured, are contemplated within the scope of the present invention. In each case, the biological disc graft 10 retains the layered structure of having a fibrocartilage layer 12 natively attached to at least one bone end plate 16. As each joint has different widths, the biological disc graft 10 is selected for a desired width, such as a width of about 1 mm, 2 mm, 3 mm, 4 mm, 5 mm, 6 mm, 7 mm, 8 mm, 9 mm, and 10 mm.

The invention also includes a kit comprising one or more implant graft and/or one or more components useful to perform the implantation procedure. For example, in addition to the kit including one or more replacement disc grafts, the kit can further include one or more additional components, such as rongeurs, curettes, distractor instruments, and the like. In certain embodiments, the one or more instruments of the kit are sterile and contained in one or more individual sterile packages. The sterile kit described herein is thus immediately ready for surgery upon removal from the packages without pre-operation processing. In certain embodiments, the kit may include instructional material that describes, for instance, suggestions for determining the proper sized disc graft and/or suggestions regarding the method of insertion. Instructional material may include a publication, a recording, a diagram, or any other medium of expression which can be used to communicate the usefulness of the graft or implant kit described herein. The instructional material of the kit of the invention may, for example, be affixed to a package which contains one or more instruments which may be necessary for the desired procedure. Alternatively, the instructional material may be shipped separately from the package.

The disclosures of each and every patent, patent application, and publication cited herein are hereby incorporated herein by reference in their entirety. While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed is:

1. A minimally invasive method for implanting a biological disc graft to treat back or neck pain, the method comprising:
    providing a biological disc graft comprising a first and a second bone endplate, a fibrocartilage layer positioned between the first and the second bone endplate, wherein the fibrocartilage layer and the bone endplates are sourced from a pubic symphysis joint, and wherein the bone and fibrocartilage layer are decellularized;
    making an incision in an annulus fibrosus of an intervertebral disc;
    removing a volume of nucleus pulposus equal to a volume of the biological disc graft; and
    inserting the biological disc graft into the space previously occupied by the volume of nucleus pulposus.

2. The method of claim 1, wherein the incision is made laterally, anteriorly, or posteriorly to the intervertebral disc.

3. A method for making the biological disc graft of claim 1, the method comprising:
    isolating a pubic symphysis joint containing fibrocartilage from a cadaver, such that the fibrocartilage includes a portion of bone on both sides of the fibrocartilage;
    milling the isolated joint to a desired thickness and shape; and
    decellularizing the isolated joint.

4. The method of claim 3, wherein the biological disc graft is milled to fit within the intervertebral disc space.

5. The method of claim 3, further comprising capping at least one of the bone portions with a push-to-lock mechanism.

6. A method for the total replacement of an intervertebral disc using a biological disc graft, the method comprising:
    providing a biological disc graft comprising a first and a second bone endplate, a fibrocartilage layer positioned between the first and the second bone endplate, wherein the fibrocartilage layer and the bone endplates are sourced from a pubic symphysis joint, and wherein the bone and fibrocartilage layer are decellularized;
    removing an annulus fibrosus and nucleus pulposus of the intervertebral disc;
    removing cartilaginous endplates of vertebral bodies above and below the intervertebral disc; and
    inserting the biological disc graft into the intervertebral disc space;
    wherein the bone endplates of the biological disc graft are seated in the space previously occupied by the cartilaginous endplates.

7. A method for the total replacement of a joint using a biological disc graft, the method comprising:
    providing a biological disc graft comprising a first and a second bone endplate, a fibrocartilage layer positioned between the first and the second bone endplate, wherein the fibrocartilage layer and the bone endplates are sourced from a pubic symphysis joint, and wherein the bone and fibrocartilage layer are decellularized;
    removing cartilaginous endplates of bones above and below the joint; and inserting the biological disc graft into the joint space.

8. The method of claim 7, wherein the joint is selected from the group consisting of: a carpometacarpal joint, a metacarpophalangeal joint, a interphalangeal joint, a meta-tarsal phalangeal joint, a wrist-bone articulation joint, a tarsal-metatarsal joint, a calcaneo-cuboid joint, a cuenonavicular joint, a acromio-clavicular joint, a sterno-clavicular joint, a spinal facet joint, a talar joint, a talonavicular joint, and a talo-calcaneal joint.

9. A method for making the biological disc graft of claim 6, the method comprising:
    isolating a pubic symphysis joint containing fibrocartilage from a cadaver, such that the fibrocartilage includes a portion of bone on both sides of the fibrocartilage;
    milling the isolated joint to a desired thickness and shape; and
    decellularizing the isolated joint.

10. The method of claim 9, wherein the biological disc graft is milled to fit within the intervertebral disc space.

11. The method of claim 10, further comprising capping at least one of the bone portions with a push-to-lock mechanism.

12. A method for making the biological disc graft of claim 7, the method comprising:
  isolating a pubic symphysis joint containing fibrocartilage from a cadaver, such that the fibrocartilage includes a portion of bone on both sides of the fibrocartilage;
  milling the isolated joint to a desired thickness and shape; and
  decellularizing the isolated joint.

13. The method of claim 12, wherein the biological disc graft is milled to fit within a joint space.

14. The method of claim 13, wherein the joint is selected from the group consisting of: a carpometacarpal joint, a metacarpophalangeal joint, a interphalangeal joint, a metatarsal phalangeal joint, a wrist-bone articulation joint, a tarsal-metatarsal joint, a calcaneo-cuboid joint, a cuenonavicular joint, a acromio-clavicular joint, a sterno-clavicular joint, a spinal facet joint, a talar joint, a talonavicular joint, and a talo-calcaneal joint.

* * * * *